(12) United States Patent
Freymiller et al.

(10) Patent No.: US 9,927,382 B2
(45) Date of Patent: Mar. 27, 2018

(54) FLAME SENSE ASSEMBLY WITH GROUND SCREEN

(71) Applicant: Carrier Commercial Refrigeration, Inc., Farmington, CT (US)

(72) Inventors: Otley Dwight Freymiller, Deerfield, WI (US); Dennis J. Nelson, Rockford, IL (US); Ronald J. Glavan, Rockton, IL (US)

(73) Assignee: CARRIER COMMERCIAL REFRIGERATION, INC., Farmington, CT (US)

( * ) Notice: Subject to any disclaimer, the term of this patent is extended or adjusted under 35 U.S.C. 154(b) by 9 days.

(21) Appl. No.: 14/907,353

(22) PCT Filed: May 30, 2014

(86) PCT No.: PCT/US2014/040133
§ 371 (c)(1),
(2) Date: Jan. 25, 2016

(87) PCT Pub. No.: WO2015/017018
PCT Pub. Date: Feb. 5, 2015

(65) Prior Publication Data
US 2016/0169823 A1    Jun. 16, 2016

Related U.S. Application Data

(60) Provisional application No. 61/860,977, filed on Aug. 1, 2013.

(51) Int. Cl.
*G01N 27/02*    (2006.01)
*F23N 5/00*    (2006.01)
(Continued)

(52) U.S. Cl.
CPC ............. *G01N 27/028* (2013.01); *F23N 5/12* (2013.01); *F23Q 3/006* (2013.01); *F23N 2029/00* (2013.01)

(58) Field of Classification Search
CPC combination set(s) only.
See application file for complete search history.

(56) References Cited

U.S. PATENT DOCUMENTS 4,298,336 A    11/1981    Riehl
4,919,609 A    4/1990    Sarkisian et al.
(Continued)

FOREIGN PATENT DOCUMENTS

CN    201944897 U    8/2011
JP    2004340428 A    12/2004

OTHER PUBLICATIONS

International Search Report for application PCT/US2014/040133, dated Sep. 19, 2014, 5 pages.
(Continued)

*Primary Examiner* — Minh Phan
(74) *Attorney, Agent, or Firm* — Cantor Colburn LLP

(57) ABSTRACT

A flame sense assembly (100) includes a flame sense electrode having a sense rod (108), at least a portion of the sense rod (108) for placement in a flame area; and an electrically conductive ground screen (110) for electrical connection to ground, at least a portion of the ground screen (110) for placement in the flame area; wherein the ground screen (110) is positioned relative to the sense rod (108) to allow an electric current to pass between the sense rod (108) to the ground screen (110) in the presence of a flame.

13 Claims, 4 Drawing Sheets

(51) Int. Cl.
    *F23N 5/12*     (2006.01)
    *F23Q 3/00*     (2006.01)

(56) References Cited

U.S. PATENT DOCUMENTS

| | | |
|---|---|---|
| 5,538,416 A | 7/1996 | Peterson |
| 5,548,277 A | 8/1996 | Wild |
| 5,720,604 A | 2/1998 | Kelly |
| 5,741,129 A | 4/1998 | Li |
| 6,749,424 B1 | 6/2004 | Kahler |
| 6,794,771 B2 | 9/2004 | Orloff |
| 7,327,269 B2 | 2/2008 | Kiarostami |
| 7,690,916 B2 | 4/2010 | Bulthaup |
| 7,764,182 B2 | 7/2010 | Chian et al. |
| 7,800,508 B2 | 9/2010 | Chian et al. |
| 7,806,682 B2 | 10/2010 | Cueva |
| 8,310,801 B2 | 11/2012 | McDonald et al. |
| 2010/0291494 A1 | 11/2010 | Branecky et al. |
| 2011/0148274 A1 | 6/2011 | Ernst et al. |
| 2011/0247604 A1 | 10/2011 | Anderson et al. |
| 2011/0250546 A1 | 10/2011 | Anderson |
| 2012/0028199 A1 | 2/2012 | Boguszewski et al. |
| 2012/0052454 A1 | 3/2012 | Roy et al. |
| 2012/0288806 A1 | 11/2012 | Racaj |
| 2013/0022932 A1 | 1/2013 | Kraus et al. |

OTHER PUBLICATIONS

Written Opinion for application PCT/US2014/040133, dated Sep. 19, 2014, 5 pages.

FLAME SENSE ASSEMBLY WITH GROUND SCREEN

FIELD OF INVENTION

The subject matter disclosed herein relates generally to the flame sensors, and more particularly, to a flame sense assembly having a ground screen.

BACKGROUND

Existing flame sensors rely on a phenomenon known as flame rectification to detect the presence of a flame. In such flame sensors, a sensing rod and an electrical ground are positioned in a flame area corresponding to an anticipated location of a flame. The presence of the flame provides an electrically conductive path wherein current may flow. A controller may induce an alternating current on this path. This alternating current is biased by the flame ions, thereby creating a sensible DC offset voltage in the AC signal.

In existing systems, the electrical ground is provided by the flame source, such as an electrically grounded, metal burner. Some burners, such as ceramic burners, are not electrically conductive and cannot serve as an electrical ground. In such installations, a ground rod is positioned proximate the sensing rod. The ground rod has limited surface area, which can result in a failure of a controller to detect the presence of a flame, even when a flame is present.

SUMMARY

According to an exemplary embodiment, a flame sense assembly includes a flame sense electrode having a sense rod, at least a portion of the sense rod for placement in a flame area; and an electrically conductive ground screen for electrical connection to ground, at least a portion of the ground screen for placement in the flame area; wherein the ground screen is positioned relative to the sense rod to allow an electric current to pass between the sense rod to the ground screen in the presence of a flame.

Other aspects, features, and techniques of embodiments of the invention will become more apparent from the following description taken in conjunction with the drawings.

BRIEF DESCRIPTION OF THE DRAWINGS

Referring now to the drawings wherein like elements are numbered alike in the FIGURES.

DETAILED DESCRIPTION

Figure 1:
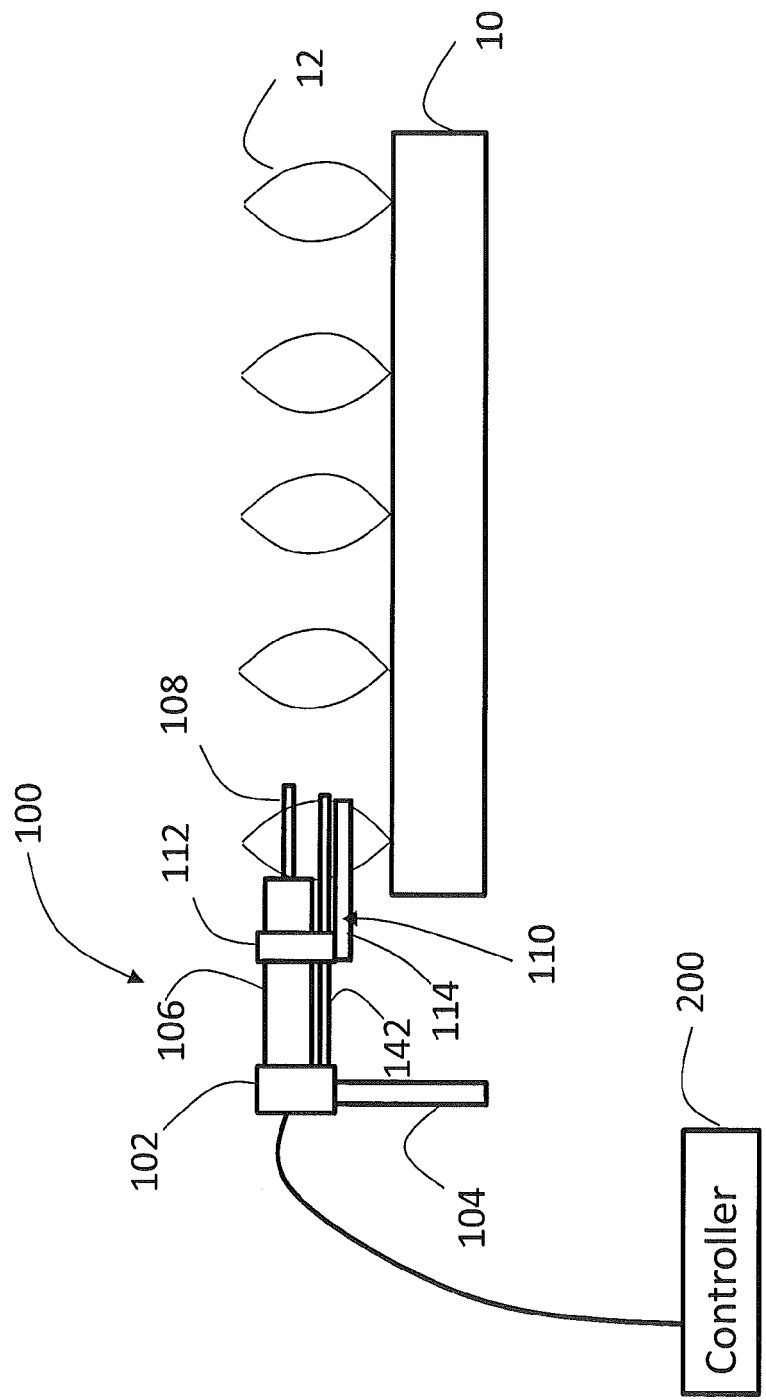
FIG. 1 depicts a burner and flame sense assembly in an exemplary embodiment.

FIG. 1 depicts a burner 10 and flame sense assembly 100 in an exemplary embodiment. Burner 10 is non-electrically conductive (e.g., ceramic) and provides one or more flames 12. Burner 10 may be part of a cooking appliance (e.g., a grill), an air heating unit (e.g., a furnace burner), or any other apparatus. Exemplary embodiments described herein refer to burner 10 being part of a grill. It is understood that embodiments are not limited to use in a grill.

Flame sense assembly 100 includes an electrically conductive mounting bracket 102 mounted to an electrically conductive surface 104 of the grill housing. Surface 104 is electrically grounded, and bracket 102 is electrically grounded via connection with surface 104. Flame sense assembly 100 includes a flame sense electrode including a body 106 supported by bracket 102. Body 106 is insulative (e.g., ceramic). Sense rod 108 is positioned internal to body 106 and extends from a distal end of body 106. Sense rod 108 is electrically conductive (e.g., iron-chromium-aluminum).

A ground screen 110 is electrically conductive (e.g., iron-chromium-aluminum) and is supported, at least in part, by body 106. Ground screen 110 includes a first portion positioned 112 about body 106 and a second portion 114, that extends away from body 106. Second portion 114 is generally planar, and includes openings for allowing flame 12 to pass through second portion 114. Both the ground screen 110 and the sense rod 108 are positioned in a flame area where flame 12 from burner 10 will be present. Ground screen 110 is shown as positioned beneath sense rod 108, but it is understood that ground screen 110 may be located at other locations, as long as the ground screen 110 and sense rod 108 are in the flame area.

A ground rod 142 is a conductive element (e.g., iron-chromium-aluminum) electrically connected to the ground screen 110 and bracket 102. Ground rod 142 serves to electrically ground the ground screen 110 and also provides a spark gap for sense rod 108 if sense rod 108 is a spark/sense rod. In other embodiments, ground rod 142 may be eliminated and ground screen 110 may extend to bracket 102 to electrically connect ground screen 110 to grounded bracket 102.

Controller 200 is connected to sense rod 108 by an electrical connection. In an exemplary embodiment, controller 200 monitors current flow between sense rod 108 and ground screen 110 to determine if a flame is present. Ground screen 110 provides an enhanced electrical ground area to provide for more accurate detection of the presence of flame 12.

Figure 2:
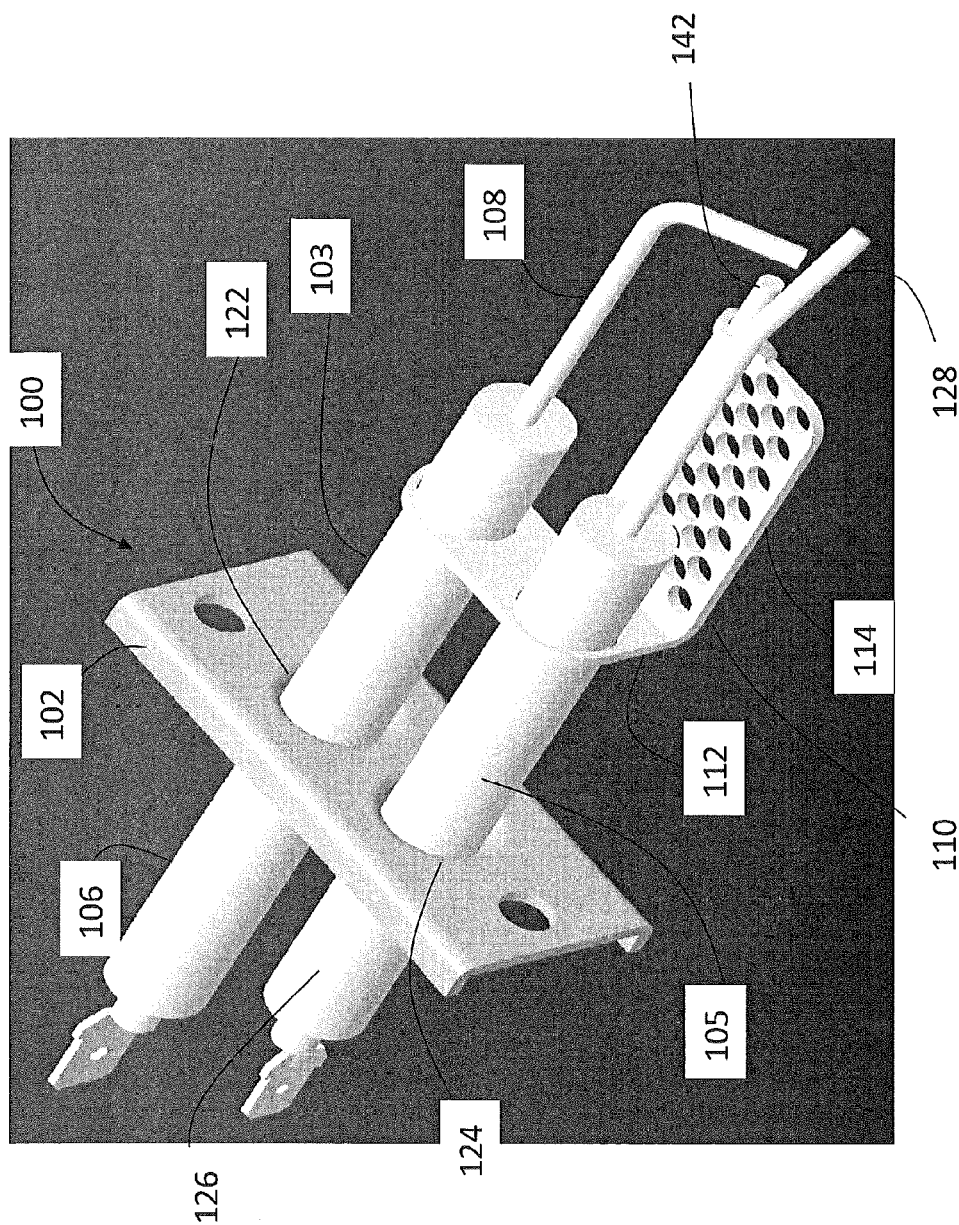
FIG. 2 depicts a flame sense assembly in an exemplary embodiment.

FIG. 2 depicts a flame sense assembly 100 in an exemplary embodiment. Flame sense assembly 100 includes bracket 102 having a first opening 122 for receiving a first flame sense electrode 103. The first flame sense electrode 103 includes body 106 and sense rod 108. Bracket 102 has a second opening 124 for receiving a second flame sense electrode 105. Second flame sense electrode 105 includes body 126 and sense rod 128. Sense rod 128 is positioned internal to body 126 and extends from a distal end of body 126. In exemplary embodiments, first flame sense electrode 103 is dual purpose flame sense electrode, providing both a spark and enabling flame presence sensing. Second flame sense electrode 105 satisfies requirements mandating a standalone (e.g., non-sparking) flame sense electrode. First flame sense electrode 103 and second flame sense electrode 105 may be supported by bracket 102 by an interference fit.

Figure 3:
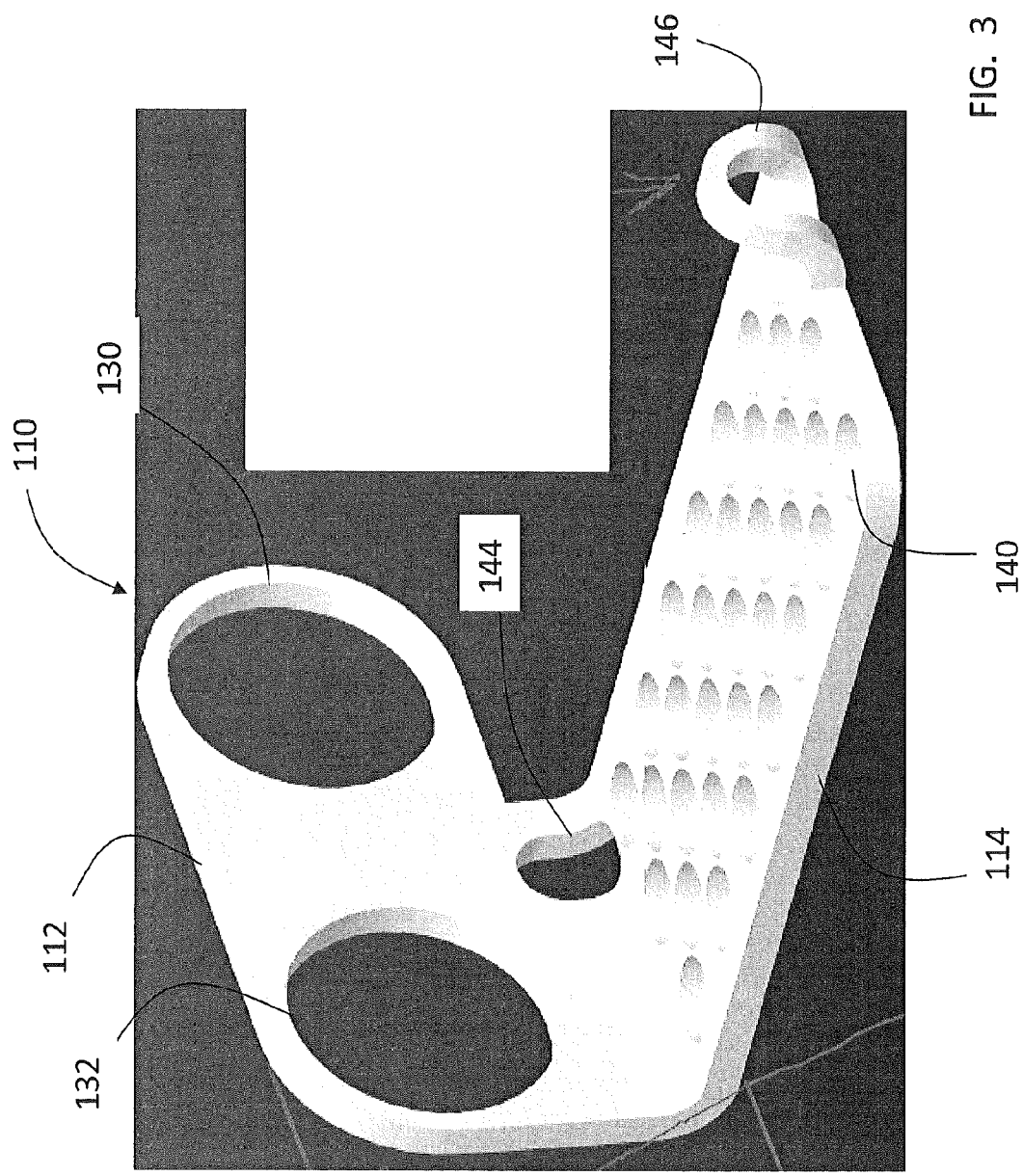
FIG. 3 depicts a ground screen in an exemplary embodiment.

Referring to FIG. 3, ground screen 110 includes first portion 112 having a first opening 130 for receiving first flame sense electrode 103 and a second opening 132 for receiving second flame sense electrode 105. Second portion 114 of ground screen 110 is generally perpendicular to first portion 112. The orientation of second portion 114 to first portion 112 may vary in exemplary embodiments. Second portion 114 includes at least one opening 140 formed thorough second portion 114. The openings 140 allow flame 12 to pass through ground screen 110 so as to not interfere with operation of burner 10.

Ground screen 110 is electrically connected to ground rod 142. Ground rod 142 has a distal end positioned proximate to a distal end of sense rod 108. Ground rod 142 is a cylindrical element extending from bracket 102 and through an opening 144 of first portion 112 of ground screen 110. Ground rod 142 may be positioned in a u-shaped collar 146 formed at a distal end of second portion 114 of ground screen 110. Ground rod 142 may be electrically and mechanically connected to ground screen 110 by tack welding at one or more locations. When igniting burner 10, a voltage is applied to sense rod 108, causing a spark across the gap between sense rod 108 and ground rod 142 to ignite fuel (e.g., air-gas) emitted from burner 10.

Figure 4:
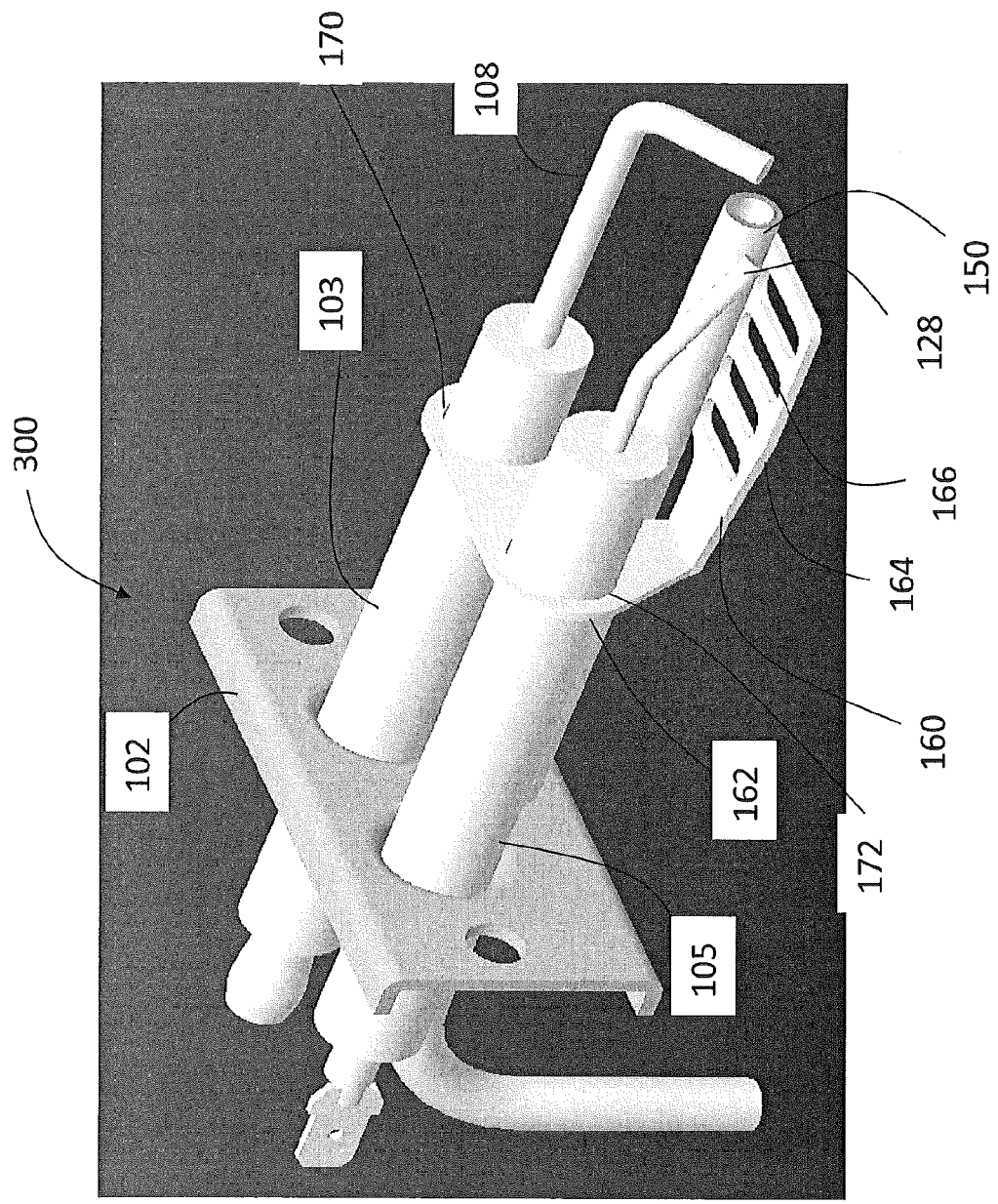
FIG. 4 depicts a flame sense assembly in an exemplary embodiment.

FIG. 4 depicts a flame sense assembly 300 in another exemplary embodiment. In FIG. 4, the ground rod is provided by a pilot tube 150. Pilot tube 150 is a conductive material (e.g., ferritic stainless steel) that provides fuel for establishing a pilot flame prior to ignition of burner 10. Pilot tube 150 is grounded in the housing of the grill. Distal end of pilot tube 150 is located proximate to a distal end of sense rod 108 to define a spark gap.

Ground screen 160 includes a first portion 162 and second portion 164, similar to those first portion 112 and second portion 114 of ground screen 110. First portion 162 includes openings 170 and 172 for receiving first flame sense electrode 103 and second flame sense electrode 105, respectively. Second portion 164 includes one or more openings 166. Openings 166 allow flame 12 to pass through ground screen 160 so as to not interfere with operation of burner 10. Ground screen 160 is mechanically and electrically connected to pilot tube 150 (e.g., by tack welding), thereby grounding ground screen 160.

Embodiments include a ground screen providing an increased surface area of the electrical ground element of a flame sense electrode. This increases the strength of the rectified flame signal and reduces the opportunity for a controller to fail to recognize a valid flame (i.e., a false flame ignition failure). In the embodiments shown herein, the ground screen is generally planar, but embodiments are not limited to this configuration. The ground screen may be polygonal, whether in a single plane, or curved about one or more axes. The second portion (114, 164) of the ground screen has a length, width and height (thickness), with the length and width each being greater than the height. The ground screen has a surface area such that a flame detection signal is generated when a flame is present.

Embodiments also control the spark gap by rigidly connecting the sense rod and ground rod near the spark gap location. In service, the spark gap may otherwise open up due to deformation over time and result in a failure to spark and ignite the fuel.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. Many modifications, variations, alterations, substitutions, or equivalent arrangement not hereto described will be apparent to those of ordinary skill in the art without departing from the scope and spirit of the invention. Additionally, while the various embodiments of the invention have been described, it is to be understood that aspects of the invention may include only some of the described embodiments and that various aspects of the invention, although described in conjunction with one exemplary embodiment may be used or adapted for use with other embodiments even if not expressly stated. Accordingly, the invention is not to be seen as being limited by the foregoing description, but is only limited by the scope of the appended claims.

The invention claimed is:

1. A flame sense assembly comprising:
   a flame sense electrode having a sense rod, at least a portion of the sense rod for placement in a flame area; and
   an electrically conductive ground screen for electrical connection to ground, at least a portion of the ground screen for placement in the flame area;
   wherein the ground screen is positioned relative to the sense rod to allow an electric current to pass between the sense rod to the ground screen in the presence of a flame;
   wherein the ground screen includes a first portion having a first opening for receiving the flame sense electrode and a second portion extending from the first portion, at least part of the second portion for placement in the flame area;
   a second flame sense electrode having a second sense rod, at least a portion of the second sense rod for placement in the flame area;
   the first portion of the ground screen having a second opening for receiving the second flame sense electrode.

2. The flame sense assembly of claim 1 wherein:
   the second portion of the ground screen includes at least one opening therethrough for allowing passage of a flame.

3. The flame sense assembly of claim 1 further comprising:
   a ground rod for electrically connecting the ground screen to electrical ground.

4. The flame sense assembly of claim 3 wherein:
   the ground rod is mechanically secured to the ground screen.

5. The flame sense assembly of claim 3 further comprising:
   an electrically conductive bracket for electrical connection to an electrically grounded housing, the ground rod electrically connected to the bracket.

6. The flame sense assembly of claim 3 wherein:
   the ground rod is positioned proximate a distal end of the sense rod to define a spark gap.

7. The flame sense assembly of claim 3 wherein:
   the ground rod is a pilot tube, the pilot tube to provide fuel for a pilot flame.

8. The flame sense assembly of claim 7 wherein:
   the pilot tube is positioned proximate a distal end of the sense rod to define a spark gap.

9. The flame sense assembly of claim 7 wherein:
   the ground screen is mechanically secured to the pilot tube.

10. The flame sense assembly of claim 1 further comprising:
    an electrically conductive bracket for electrical connection to an electrically grounded housing, the ground screen electrically connected to the bracket.

11. The flame sense assembly of claim 1 wherein: the second portion of the ground screen is planar.

12. The flame sense assembly of claim 1 wherein:
    the second portion of the ground screen has a length, width and height, the length and width each being greater than the height.

13. The flame sense assembly of claim 1 wherein:
the second portion of the ground screen is polygonal.

\* \* \* \* \*